United States Patent
Ollivier (10) Patent No.: US 9,427,576 B2
(45) Date of Patent: Aug. 30, 2016

(54) EPICARDIAL SCREW LEAD FOR STIMULATION / DEFIBRILLATION IMPLANTABLE BY A GUIDE CATHETER INSERTED INTO A PERICARDIAL SPACE

(75) Inventor: Jean-Francois Ollivier, Villers le Bacle (FR)

(73) Assignee: SORIN CRM SAS, Clamart (FR)

(*) Notice: Subject to any disclaimer, the term of this patent is extended or adjusted under 35 U.S.C. 154(b) by 248 days.

(21) Appl. No.: 12/900,223

(22) Filed: Oct. 7, 2010

(65) Prior Publication Data
US 2011/0082466 A1    Apr. 7, 2011

(30) Foreign Application Priority Data
Oct. 7, 2009 (FR) ...................................... 09 56982

(51) Int. Cl.
*A61B 17/00* (2006.01)
*A61N 1/05* (2006.01)
*A61M 25/00* (2006.01)
*A61M 25/06* (2006.01)

(52) U.S. Cl.
CPC ........ *A61N 1/0587* (2013.01); *A61M 25/0041* (2013.01); *A61M 25/0662* (2013.01)

(58) Field of Classification Search
CPC ............... A61M 25/00; A61M 25/06; A61M 25/0041; A61M 25/0662; A61N 1/056; A61N 1/059; A61N 1/0595; A61N 1/0592; A61N 1/0597; A61N 1/04; A61N 1/0424; A61N 1/044; A61N 1/205; A61B 17/02; A61B 1/32
USPC ............... 607/119, 121, 122, 123, 126, 127; 606/130, 131
See application file for complete search history.

(56) References Cited

U.S. PATENT DOCUMENTS

| | | | | |
|---|---|---|---|---|
| 3,915,174 A | * | 10/1975 | Preston | 607/9 |
| 4,602,645 A | * | 7/1986 | Barrington et al. | 607/123 |
| 4,882,777 A | * | 11/1989 | Narula | 604/532 |
| 5,330,496 A | | 7/1994 | Alferness | |
| 5,336,252 A | * | 8/1994 | Cohen | 607/119 |
| 6,002,969 A | * | 12/1999 | Machek et al. | 607/122 |

(Continued)

FOREIGN PATENT DOCUMENTS

| | | |
|---|---|---|
| WO | WO 03086502 | 10/2003 |
| WO | WO 2006116719 | 11/2006 |
| WO | WO 2007115158 | 10/2007 |

OTHER PUBLICATIONS

Foreign Search Report (Annexe Au Rapport De Recherche Preliminaire Relatif A La Demande De Brevet Francais No. FR0956982 FA727559, Jun. 11, 2010.

*Primary Examiner* — Jonathan Miles
*Assistant Examiner* — George J Ulsh
(74) *Attorney, Agent, or Firm* — Foley & Lardner LLP (57) ABSTRACT

An epicardial screw lead for stimulation/defibrillation implantable by a guide-catheter inserted into the pericardial space is described. The lead is a monodiameter lead with a helical anchoring screw extending axially of the lead body. The guide-catheter (24) has a pre-shaped tube having, in the absence of stress, a first bend (26) for supporting the lead body on the outer wall of the pericardial space (38), and a second bend (28) for orienting the end of the guide-catheter tube in the direction of the outer wall of the myocardium (34) and keeping the axis of the anchoring screw (14) in that same direction during a combined movement of screwing and insertion of the lead head.

18 Claims, 3 Drawing Sheets

(56) References Cited

U.S. PATENT DOCUMENTS

| | | | |
|---|---|---|---|
| 6,385,492 B1 * | 5/2002 | Ollivier | A61N 1/056 607/122 |
| 6,408,214 B1 * | 6/2002 | Williams et al. | 607/122 |
| 7,867,218 B1 * | 1/2011 | Voda | 604/532 |
| 2002/0123784 A1 * | 9/2002 | Westendorp | 607/122 |
| 2003/0167082 A1 * | 9/2003 | Ollivier et al. | 607/126 |
| 2004/0015193 A1 | 1/2004 | Lamson et al. | |
| 2007/0100409 A1 | 5/2007 | Worley et al. | |
| 2007/0100510 A1 | 5/2007 | Lamson et al. | |
| 2007/0203555 A1 * | 8/2007 | Williaims | 607/122 |
| 2007/0239247 A1 | 10/2007 | Camps et al. | |
| 2008/0208128 A1 | 8/2008 | Guo et al. | |
| 2008/0208166 A1 * | 8/2008 | Goode et al. | 604/510 |
| 2010/0010469 A1 | 1/2010 | Goode et al. | |

\* cited by examiner

EPICARDIAL SCREW LEAD FOR STIMULATION / DEFIBRILLATION IMPLANTABLE BY A GUIDE CATHETER INSERTED INTO A PERICARDIAL SPACE

CROSS-REFERENCE

This application claims the benefit of French application number 09 56982, filed Oct. 7, 2009, the entire contents of which are hereby incorporated by reference.

FIELD

The invention relates to "active implantable medical devices" as defined by the 20 Jun. 1990 Directive 90/385/EEC of the Council of the European Communities, particularly to implantable devices that monitor a patient's heart rhythm and deliver, if necessary, electrical stimulation or resynchronization pulses at the patient's heart, and more specifically to "epicardial" leads that are fixed on the outer wall of the patient's heart. Epicardial leads are contrasted with "endocardial" leads that are introduced via the patient's venous system and inserted in a cavity of the patient's heart.

It should be understood that, although the present invention is, in some examples here, described with reference to pacing leads that deliver low energy pulses for anti-bradycardia or resynchronization therapies, the present invention also applies to epicardial leads that deliver to the patient's heart high energy electrical shocks for cardioversion/defibrillation to alleviate or terminate a tachyarrhythmia. As used herein, the term "stimulation/defibrillation lead" describes any type of lead used for any of these purposes.

BACKGROUND

Epicardial leads may be prescribed for the stimulation of the left ventricle, as an alternative to pacing leads implanted via the coronary sinus, whose implantation requires a delicate approach and suffers various drawbacks.

Unlike endocardial leads introduced via a patient's venous network, the implantation of an epicardial lead constitutes a more invasive operation, usually requiring general anesthesia and surgical techniques. A chest surgeon incises the patient's thorax to gain an access to the "pericardial sac" (the pericardium being the fibroserous envelope that surrounds the heart) and the myocardium itself and to fix the epicardial lead on the external wall of the myocardium, by suturing or screwing.

Several types of epicardial leads have been proposed, but they have a number of drawbacks.

One type of commonly-used epicardial leads is a sutured lead. This sutured type of epicardial leads is very stable, but requires a broad access to allow a work area for suturing the lead by a surgeon. In addition, the area of possible implantation is restricted to the vicinity of the incision in the chest.

It is also known that a screw lead is used to secure an epicardial lead. The screwing may be done directly, but the work area is limited in the same manner as a sutured lead. The screwing may also be done using an implantation tool with a handle, a telescopic support tube, and an articulated head on which the screw lead is mounted. In this case, the surgeon may gain an access to an implantation site beyond the incision, but the possible area of implantation is nevertheless limited by the rigidity of the support tube, and the diameter of the support tube (e.g., 40 French) that the surgeon must insert ahead into the curved pericardial space.

Furthermore, the existing screw leads have a low electrical performance (e.g., pacing threshold peaking, low impedance) due to the large size of the screw. The low electrical performance is desirable to withstand the implantation conditions, but it does not provide a satisfactory current density for impedance measurement. In addition, these screws are relatively traumatic to the tissue, and increase a risk of locally creating reactive fibrosis.

It is important, however, from a mechanical point of view, that the screws of the known leads be oversized, to accommodate the high stress on the screw exerted during implantation, with large implantation accessories that offer very little sensitivity to rotation. The lead head is subjected to a high mechanical stress due to its large displacement, combined with a radial traction exerted through the lead body. The mechanical anchorage of the lead head on the myocardium should be able to resist these mechanical constraints.

Regarding being oversized, the diameter of the screw of an epicardial lead is in the order of 4 to 5 mm compared to 1.2 mm for the screw of a typical endocardial lead; the length of the screw is in the order of 5 to 6 mm for an epicardial lead compared to 1.6 to 1.8 mm for a typical endocardial lead; the wire diameter of the epicardial lead is 0.6 mm compared to 0.3 mm of a typical endocardial lead.

Another feature that is common to known epicardial leads is that the lead body, a sheath connecting the lead head to a pacing generator, is connected at a right angle to the lead head. In other words, the axis of the sheath is perpendicular to the axis of the screw. Consequently, the lead system requires a large volume, thus is traumatic in the area of the stimulation site.

In addition, the geometry and configuration of these epicardial leads prevent the surgeon from extracting them by a simple screwing and require a major surgical operation for extraction.

U.S. Published Application No. 2008/0208166 A1 describes a pre-shaped endocardial catheter for delivery with a double curvature forming a heart-wrapping segment that wraps the outer surface of the heart by covering it over most of the epicardium.

Such a catheter, if combined with a screw lead, would limit the screwing capacity as well as the capacity to move over a large area on the surface of the heart. Indeed, the broad curves of the heart-wrapping structure tend to coincide with the external shape of the heart, by the principle of least energy. The result is a given equilibrium position (i.e., at a given implantation site) for a given curvature. Hence, there is a need for several endocardial catheter models with different curvatures if several possible implantation sites are required.

OBJECTS AND SUMMARY

It is therefore an object of the present invention to propose a new type of an epicardial lead, and an accessory tool for its implantation. It is a further object of the present invention to provide an epicardial lead that overcomes one or more of the drawbacks mentioned above, particularly by:

reducing the size of the incision required to access the heart; for example, to a simple puncture;

miniaturizing the lead head to make it less traumatic;

miniaturizing the implantation accessory tool, so as to provide a greater sensitivity to the practitioner and make the intervention less invasive;

maximizing the working area around the point of introduction into the pericardial envelope, and thus the extent of potential stimulation sites;

increasing maneuverability for the site selection;

allowing an access path that does not require tunneling;

offering a "mapping" to test the electrical response of the potential implantation site before the final screwing of the lead;

ensuring a quality mechanical fixing that is less traumatic to the tissues;

increasing the electrical performance;

allowing a simple extraction;

providing an "isodiameter" (or "monodiameter") configuration that is compatible with the current surgical techniques of implantation.

Broadly, the present invention is directed toward an epicardial lead that is of a screw lead type, in which the screw extends into an extension of the lead body (one that is not at 90° with respect to the lead body), and in which the screw has a size and characteristics comparable to that of an endocardial lead screw.

The present invention also proposes an accessory tool for the implantation of such a lead on the external wall of the myocardium. The accessory tool is a guide-catheter in which the lead is introduced. The guide-catheter can be introduced into the pericardial space by a simple puncture (for example, without an incision of the pericardial envelope). The guide-catheter is flexible and has an atraumatic soft tip so that it can be moved over and around the surface of the myocardium to safely "navigate" on the epicardium to choose a stimulation site. Advantageously, the chosen stimulation site may be relatively far from the puncture site, relatively easily providing the point of access to the pericardial space as compared with prior known epicardial leads.

The present invention proposes advantages over the disclosure of U.S. Patent Publication 2008/0208166 A1 by an improved guide-catheter allowing:

to freely navigate in the pericardial space without being bothered by the principle of least energy;

once the stimulation site is selected, to guide the tip of the curvature of support in the correct direction (leaving only the possibility of two stable angular positions, easily distinguishable, namely: towards the epicardium or towards the pericardial sac); and to secure the selected stimulation site by the application of a manual torque on the proximal end.

Another technique, described in WO 03/086502 A2, implements a guide-wire that is previously inserted into the pericardial space, and anchored at its distal end in the wall of the myocardium. A lead equipped with surface electrodes is then slipped over the guide-wire to the chosen implantation site.

If a guide-catheter that is inserted into the pericardial space were combined with a screw lead, it remains to be solved how to ensure stabilization of the guide-catheter once the stimulation site is chosen, so as to allow the screwing of the lead head to be fixed permanently.

To that purpose, the present invention provides a preformed guide-catheter with two successive bends in its distal region;

a first bend that is located farther from the distal end of the guide-catheter, is a support curve for the guide-catheter, to allow it to be supported by the outer wall of the pericardial sac as a result of a torque provided by the practitioner, and to stabilize in place the guide-catheter despite various stresses including the effect of heart beats;

a second bend that is located nearer from the distal end of the guide-catheter than the first bend, is an orientation curve to allow the axis of the anchoring screw to be turned to the outer wall of the myocardium, forming with the latter an angle sufficient to allow screwing according to a predefined angle of attack.

The lead and the guide-catheter have a relatively small cross section dimension, for example, between about 6 and 9 French. When combined as an isodiameter lead, just a simple puncture is required to introduce the guide-catheter and the lead into the pericardium without needing an incision of the pericardial sac.

Further, a mono-diameter lead facilitates its extraction by unscrewing and removing the lead, without requiring any major surgery.

Another aspect of the present invention is directed to a system including an epicardial screw lead of any type commonly used for stimulation/defibrillation, and comprising: a lead body having a sheath that is made of a deformable material; a distal end having a lead head with an electrode for stimulation/defibrillation and a helical anchoring screw to penetrate into the outer wall of the myocardium under the effect of a screw motion imparted to the lead head; and a proximal end having means for coupling the system to a generator of a medical device. The system also may include an accessory tool to implant the epicardial lead.

In accordance with a preferred embodiment of the invention, the lead is a mono-diameter lead having a helical anchoring screw extending axially of the lead head, and the accessory tool is a guide-catheter to be introduced into the pericardial space. The guide-catheter is preferably a hollow tube open at both ends having a central lumen and a distal outlet. The central lumen is sized so that the lead is insertable in and translatable within the guide-catheter between a retracted position where the lead head is flush with the distal outlet of the central lumen and a deployed position where the lead head, with the anchoring screw, emerges from the central lumen distal outlet. The hollow tube of the guide-catheter tube is preferably preformed, elastically deformable, and relatively more rigid than the sheath of the lead body, and in the absence of stress has a first bend and a second bend inscribed in two respective separate areas. The first bend has a curvature adapted to allow a support of the lead body against the outer wall of the pericardial space, and the second bend, more distal than the first bend, is a curvature that allows an orientation of the end of the guide-catheter tube in the direction of outer wall of the myocardium, and maintains the axis of the anchoring screw in this same direction during a combined movement of screwing and insertion of the lead head towards the deployed position.

The anchoring screw can be a fixed or a mobile screw, retractable into a housing in the lead head. It may be a screw including an active electrode for stimulation/defibrillation, or a passive screw, electrically decoupled from the electrode for stimulation/defibrillation.

The sheath of the lead body is preferably selected to present a sufficient torsional stiffness to enable transmission along its entire length of a rotational movement from the proximal end of the lead, for screwing the anchoring screw.

In addition, the system optionally includes a removable stylet. The removable stylet is inserted into a lumen of the lead body and moved in translation within that lumen to the lead head, and means for coupling the stylet in rotation with the lead head. The stylet preferably has a sufficient torsional rigidity to enable transmission along its entire length and to the means for coupling, of a rotating movement from the proximal end of the stylet, for screwing of the anchoring screw.

Preferably, the diameter of the guide-catheter is less than or equal to 9 French, more preferably greater than or equal to 6 French, and the lead body is less than or equal to 5 French. It should be understood that smaller dimensions could be used, provided that sufficient current density can be achieved for the desired therapeutic purposes.

Preferably, the anchoring screw includes an end portion to penetrate the outer wall of the myocardium and connected to the lead head by a transition portion that is mechanically deformable in flexion, more preferably including a part having several adjacent turns of the helical screw.

The anchoring screw also includes an active region with an electrically conductive tip, an electrically isolated extended middle portion, whose axial length is preferably less than or equal to 1 mm.

The curvatures of the first and second bends are preferably part of a parallelepiped volume with a dimension between 15×10×5 mm$^3$ and 25×15×5 mm$^3$. This volume is adequate for positioning and anchoring the screw lead in the pericardial space for maintaining and guiding the lead head through the guide-catheter.

BRIEF DESCRIPTION OF THE DRAWINGS

Further features, characteristics, and advantages of the present invention will become apparent to a person of ordinary skill in the art from the following detailed description of a pictured embodiment of the present invention, made with reference to the annexed drawings, in which:

In FIG. 7a the screw 14 is in the retracted position. In FIG. 7b the screw 14 is in the deployed position.

FIG. 8 depicts a removable stylet 44. The removable stylet 44 is inserted into a lumen 35 of the lead body 12 and moved in translation within that lumen 35 to the lead head, and means for coupling the stylet 44 in rotation with the lead head.

DETAILED DESCRIPTION

With reference to FIGS. 1-6, a preferred embodiment of the present invention will now be described. In the Figures, reference 10 refers generally to the screw lead of the assembly, according to the present invention. The screw lead 10 comprises a lead body 12 that is usually made of a polyurethane sheath 15 to minimize friction when lead body 12 is inserted into a guide-catheter 24, and to provide adequate sensitivity and torque transmission. The diameter of the sheath 15 of the lead body 12 is chosen sufficiently thin (typically less than or equal to 5 French) to be compatible with the size of the pericardial space and the diameter of the guide-catheter.

Figures 1, 2, 3, 4:
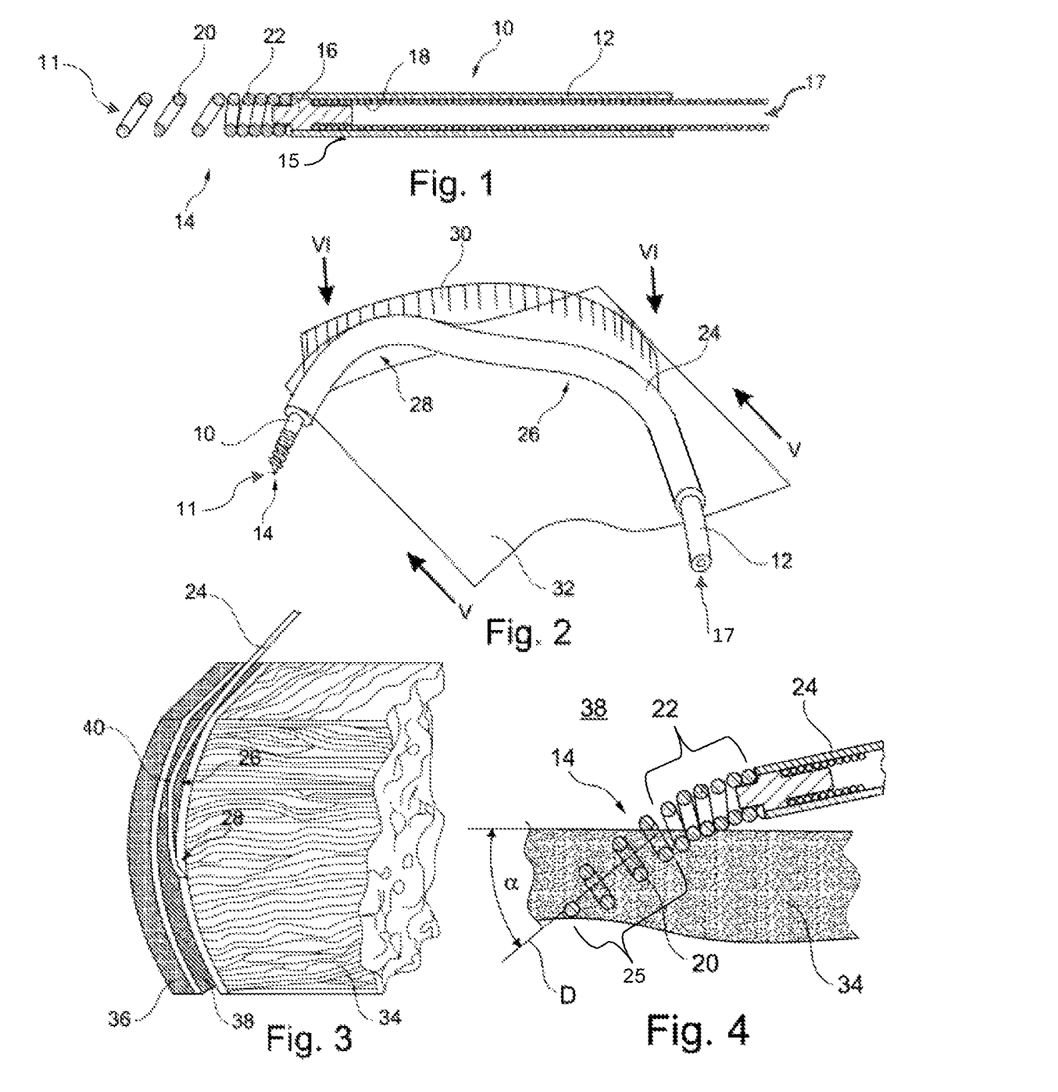
FIG. 1 is a section view of the lead head, according to the invention.
FIG. 2 is an elevated perspective view of the lead head of FIG. 1.
FIG. 3 is a partial sectional view of an envelope of the heart and showing how the catheter-lead assembly according to the invention is introduced and positioned in the pericardial sac.
FIG. 4 is a sectional view of the lead head of FIG. 1 after it has been implanted in the pericardial sac, with the screw anchored in the outer wall of the myocardium.

The screw lead 10 is terminated at its distal end 11 by a helical anchoring screw 14 made of a conductive material, connected through a metal tip 16 to an inner conductor 18. Inner conductor 18 is preferably a spiral conductor providing electrical continuity between the anchoring screw, which serves as an electrode for stimulation and/or detection, and the generator located at the proximal end 17 of screw lead 10 (not shown). It should be understood that the polyurethane sheath material and the dimension of the assembly may be chosen to provide some torsional rigidity to the lead body 12 so as to transmit torque from the proximal to the distal end and to rotate the anchoring screw 14 to penetrate into the heart tissue.

Unlike conventional epicardial leads in which the screw extends at right angle from the lead body to which it is connected, the anchoring screw 14 is an axial screw that extends along the lead body 12, thereby providing to the assembly an "isodiameter" or "monodiameter" configuration.

The anchoring screw 14 is advantageously constructed with a distal portion formed over a length of about 1.5 to 2 mm, a plurality of adjacent turns 20 connected to the lead body 12 via a mechanical transition portion having flexibility in flexion, formed by a number of adjacent turns 22 in the absence of stress on the screw.

The anchoring screw 14 is advantageously insulated over its entire length, for example, by a coating of parylene, except for the last distal millimeter that is the only electrically active part of the anchoring screw 14. This construction reduces the surface of stimulation and thus increases the current density and the electrical efficiency of the lead. This electrically active part is buried deeply into the wall of the epicardium, therefore the electric field for stimulation is concentrated to a deeper and more physiological zone, reducing the risk of a phrenic nerve stimulation.

In the illustrated embodiment, the anchoring screw 14 is an active screw, that serves (at least at its distal end) as a stimulation electrode. Alternatively, the anchoring screw 14 can be an electrically passive screw used for anchoring the lead head against the wall of the epicardium. In this latter case, the sensor head is connected to the distal end of a separately provided electrode, for example, a ring-shaped electrode for stimulation.

Figure 5:
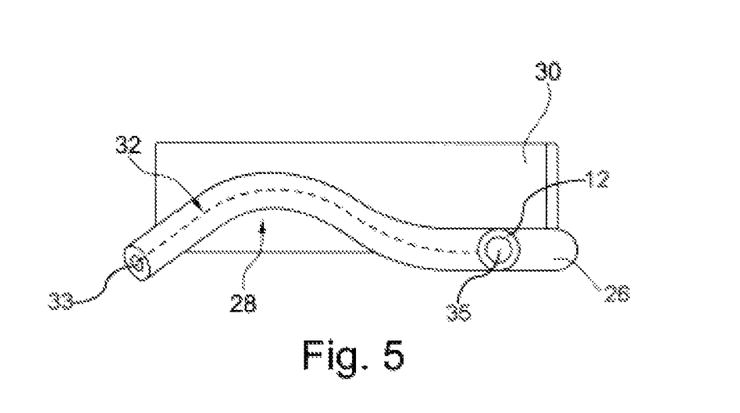
FIG. 5 is an end view taken along line V-V of FIG. 2.
Figure 6:
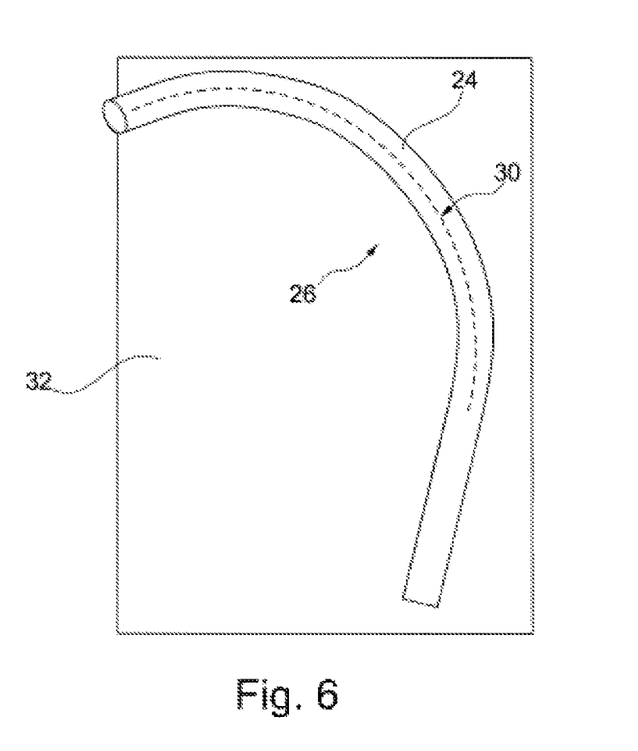
FIG. 6 is a top view taken along line VI-VI of FIG. 2.
Figure 7:
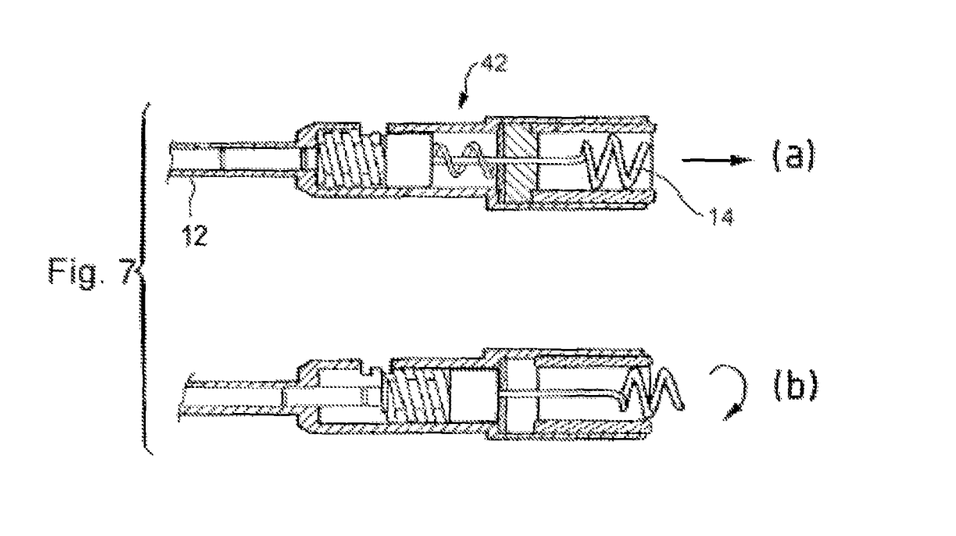
FIG. 7 depicts a lead head with a housing 42. The anchoring screw 14 can be a fixed or a mobile screw, retractable into a housing 42 in the lead head.
Figure 8:
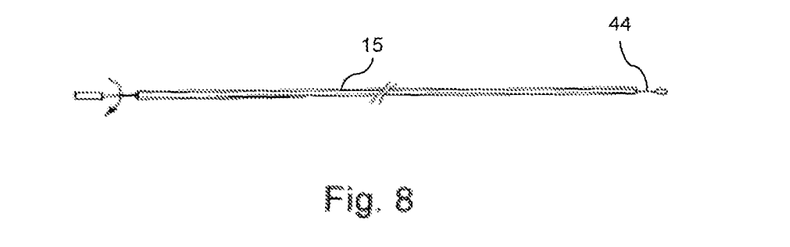

With reference to FIG. 2, the guide-catheter 24 is used for the introduction into its interior and implantation of the screw lead 10 into a stimulation. The guide-catheter is preferably a hollow tube open at both ends having a central lumen 35 and a distal outlet 33 as depicted in FIG. 5. The distal part of the guide-catheter 24 is open at its end, so as to deploy the distal end 11 of the screw lead 10 and its anchoring screws 14 by a relative axial movement of the lead body 12 inside the guide-catheter 24.

The guide-catheter 24 has at its distal end two successive bends (or curvatures) 26 and 28, respectively defining separate curvilinear surfaces 30 and 32.

The curvilinear surface 30 defines a bend 26 (herein called a "support curvature") that naturally follows a relatively spherical curve during the progression of the guide-catheter 24 into the pericardial space. Also, when an implantation site is chosen, the support curvature 26 creates a support against the inner wall of the pericardial sac in order to hold the guide-catheter 24 therein in a position in the presence of heart beats. In a preferred embodiment, the curvilinear surface 30 has a dimension (corresponding to the view of FIG. 6) in the order of 15-25 mm by 10-15 mm.

The curvilinear surface 32 defines a bend 28 (herein called an "orientation curvature") that directs the lead head, and thus the axis of the anchoring screw 14, toward the wall of the myocardium at a predefined angle of attack. In a preferred embodiment, the curvilinear surface 32 has dimensions in elevation (corresponding to the view of FIG. 5) in the order of 10-15 mm by a maximum of 5 mm.

In other words, the successive bends 26 and 28 exist within (or are defined in) a parallelepiped volume with a dimension preferably between 15×10×5 mm$^3$ and 25×15×5 mm$^3$ that is consistent with the interior dimension of the pericardial space to allow maintaining and guiding the lead head through the guide-catheter 24.

With reference to the drawings, reference 34 generally designates the myocardium or the heart muscle that is wrapped in a fibro-serous bag or "pericardial sac" 36. Pericardial sac 36 defines between the outer wall of the myocardium and its inner wall a pericardial space 38 filled with a small amount of liquid, allowing the movement of the heart inside the chest.

The diameter of the guide-catheter 24 is chosen sufficiently thin, typically between 6 French and 9 French, to allow easy navigation in the pericardial space 38. It is also possible to use a 6 French guide-catheter strengthened by a standard 9 French guide-catheter to provide a telescoping feature while increasing the rigidity of the lead body to improve monitoring, according to well known procedures for manipulating guide catheters.

In connection with the use of the system of the present invention, once a stimulation site is identified, the practitioner holds the guide-catheter 24 and applies a torque to a handle (not shown) located at the proximal end of the guide-catheter 24. Because of the curvature 26, the guide-catheter 24 comes into contact with area 40 against the outer wall of the pericardial space 38, thereby generating a resistant torque in the opposite direction. By the continuous insertion of the guide-catheter 24 into the pericardial space 38, the distal end of the guide-catheter 24 is pushed toward the outer wall of myocardium 34, and the lead is maintained in support on the selected implantation site, while following the movements by the heart beats.

The orientation curvature 28 at the distal end has the effect of directing the axis of the anchoring screw 14, not in a continuation of the pericardial space 38, but on the contrary, as shown in FIG. 4 (after withdrawal of guide catheter) into the outer wall of the myocardium 34 with a predetermined angle of attack. In this way, the anchoring and the subsequent screwing of the screw 14 are guided along a direction D according to an angle α relative to the general axial direction of the lead.

Once the stimulation site is reached, the practitioner slides the screw lead 10 within the guide-catheter 24 until the distal end of the lead and the anchoring screw 14 emerge from the corresponding end of the catheter-guide 24 (in a configuration as shown in FIG. 2). Because of the two successive curvilinear surfaces 30 and 32 of the distal end of the guide-catheter 24 described above, the distal opening of the guide-catheter 24 is directed toward the outer wall of the myocardium 34 at an attack angle α relative to the general surface of the pericardial space 38. The anchorage screw 14 is inserted into the guide-catheter 24 and is pushed toward the screw lead 10 until it deploys and emerges from the guide-catheter 24 and comes in contact with the myocardium 34.

In accordance with the present invention, it is possible to electrically test a selected contact point and validate the chosen stimulation site before finally anchoring the screw. If the chosen stimulation site is not satisfactory, the practitioner simply moves, under control, the guide-catheter 24 in the pericardial sac to another location to test a new stimulation site.

The final anchoring is obtained by imparting an axial rotation to the lead body 12 in the case of a fixed screw lead. For a pin driven lead, the final anchoring is obtained by imparting an axial rotation to the connector plug, in which at the proximal side, the connection plug is connected to a conductor extending axially within the body of the lead and the conductor is free in rotation and connected to the anchoring screw at its distal end. Another possibility is to introduce in the lumen 35 of the lead body 12 a specific screwing stylet. The screwing stylet is particularly useful when the sheath does not have a sufficient torsional rigidity to drive the anchoring screw 14 directly from the proximal end.

In another embodiment, instead of a fixed screw it is possible to use a retractable screw, a mechanism thereof is in itself known. In this embodiment, the rotation causes the deployment of the screw out of its slot, then with a continued rotation after the deployment, the screw is penetrated into the myocardium wall.

The last step is to remove the guide-catheter 24. Preferably, the removal of the guide-catheter 24 is done according to a standard procedure, preferably cutting the sheath using a slitter tool. See, for example, the description of slitting in EP 2039390 A1 and its counterpart U.S. Patent Publication 2009/0071012 assigned to ELA Medical (now known as Sorin CRM).

FIG. 4 illustrates the final and definitive configuration, when the lead screw 14 is anchored to a myocardial wall 34.

The lead head being no longer supported by the guide-catheter 24, it is articulated in the direction of the lead body through the flexible transition portion 22, thus minimizing the constraints on the pericardial sac. The end part 25 of the anchoring screw 14 penetrates the outer wall of the myocardium.

The aforementioned features and techniques of guiding the lead body using the guide-catheter offer the following advantages:

- a minimally invasive technique: access to the pericardial sac is not made through an incision, rather by a simple puncture of a single hole (e.g., 9 French in diameter) performed by a needle and expanded. The puncture is self-closing without the need for a suture reducing the risk of infection. This minimally invasive intervention can be conceivably achieved by an electrophysiologist, without requiring a surgeon;
- the ability to map a large area around the access point, and in remote areas, even opposite of the access point, because the guide-catheter can be navigated in a large area within the pericardial sac;
- atraumatic advancement of the lead head in the pericardial space compared to the currently available solutions: the search for the optimal site is performed by a secured guide-catheter by an electrophysiology catheter, or by a conventional smooth dilator and guide wire, unlike the currently available leads in which the final screw is exposed in the distal part of the implantation accessory, posing a risk of dissection of the pericardial sac and/or of the tissue surface. Navigation is also greatly facilitated by the small size of the guide-catheter 24, typically with a diameter of 6 French;
- superior electrical performance compared to currently available leads, thanks to the mechanical decoupling between the lead body 12 and the anchoring screw 14 because of the flexible transition part;

a concentration of the electrical flow in a deep region of the myocardium 34;

an excellent extraction capability, by simple unscrewing of the distal end: in particular the isodiameter nature of the lead facilitates such an extraction simply by unscrewing and removing the lead; and the mechanical simplicity of the assembly, therefore a low manufacturing cost and a high reliability.

One skilled in the art will appreciate that the present invention may be practiced by other than the embodiments described herein, which are provided for purpose of illustration, and not of limitation.

The invention claimed is:

1. An epicardial lead system comprising:
   (A) an epicardial screw lead that comprises
      a monodiameter lead body having a sheath made of a deformable material, a distal end, a distal outlet, a proximal end and a lead head, disposed at the distal end, that comprises an electrode and a retractable anchoring screw, wherein rotation of the lead body in a first direction causes deployment of the screw out of the lead body and additional rotation in the first direction after deployment causes the screw to penetrate a myocardium wall,
      wherein the lead head and the retractable anchoring screw are oriented along the same axis such that the retractable anchoring screw extends from the lead head in response to a screwing motion of the lead head; and
   (B) an accessory tool, for implantation of the epicardial lead, that comprises
      a removable guide-catheter comprising a hollow tube open at both ends and having a central lumen and a central lumen distal outlet,
      wherein the epicardial screw lead is translatable within the central lumen between a retracted position in which the epicardial screw lead is not extended out of the central lumen distal outlet, and a deployed position in which the epicardial screw lead is extended out of the central lumen distal outlet,
      wherein the hollow tube is an elastically deformable, pre-shaped tube that is relatively more rigid than the sheath of the lead body, and has, in the absence of stress, a first bend in a first curvilinear surface and a second bend in a second curvilinear surface, wherein the span along a length of the hollow tube of the first bend in the first curvilinear surface coincides with the span along the length of the hollow tube of the second bend in the second curvilinear surface, and wherein the first and the second curvilinear surfaces are defined in different planes;
      wherein the second bend is a distal orientation bend that orients the central lumen distal outlet so as to direct the epicardial screw lead at a predetermined acute angle relative to an outer wall of a myocardium; and
      wherein the first bend and second bend are within a parallelepiped volume of between 15×10×5 mm³ and 25×15×5 mm³, the first bend being proximal of the second bend and having a curvilinear surface with dimensions of 15-25 mm by 10-15 mm, and the second bend having a curvilinear surface in a different plane than the curvilinear surface of the first bend with dimensions of 10-15 mm by no more than 5 mm.

2. The system of claim 1, wherein the retractable anchoring screw is an active screw, forming said electrode for stimulation/defibrillation.

3. The system of claim 1, wherein the retractable anchoring screw is a passive screw, electrically isolated from said electrode for stimulation/defibrillation.

4. The system of claim 1, wherein the sheath of the lead body has a torsional stiffness sufficient to allow transmission along its length of a rotation movement from the proximal end of the lead body for screwing the retractable anchoring screw.

5. The system of claim 1, wherein the sheath of the lead body has sufficient torsional stiffness to enable transmission along its length of a rotation movement from the proximal end of the lead body, and in which the system further comprises:
   a removable stylet, dimensioned to be inserted into the lumen of the guide-catheter and movable in translation within that lumen up to the lead head, and
   a coupler for attaching the stylet in rotation with the lead head, said stylet having a sufficient torsional rigidity to allow transmission along its entire length and to enable screwing the retractable anchoring screw.

6. The system of claim 1, wherein the guide-catheter has a diameter of between 6 and 9 French.

7. The system of claim 1, wherein the lead body has a diameter of less than or equal to 5 French.

8. The system of claim 1, wherein the retractable anchoring screw comprises an end part portion to penetrate the outer wall of the myocardium and is connected to a transition portion mechanically deformable in flexion.

9. The system of claim 8, wherein the transition portion mechanically deformable in flexion comprises a number of adjacent turns of the projecting helical screw.

10. The system of claim 8, wherein the transition portion mechanically deformable in flexion consists of a number of adjacent turns of a projecting helical screw.

11. The system of claim 1, wherein the retractable anchoring screw comprises an end part portion to penetrate the outer wall of the myocardium, and an active region of an electrically conductive tip extending through an electrically insulated part.

12. The system of claim 11, wherein an axial length of the active region of the electrically conductive tip is at most 1 mm.

13. The system of claim 1, wherein the two separate curvilinear surfaces include a first curvilinear surface defined by the first bend in a first plane and a second curvilinear surface defined by the second bend in a second plane, and wherein the first plane is substantially perpendicular to the second plane.

14. The system of claim 1, wherein the different planes of the first and second curvilinear surfaces intersect and form an angle between the planes.

15. An accessory tool for implantation of an epicardial lead, comprising:
   a removable guide-catheter comprising a hollow tube open at both ends and having a central lumen and a central lumen distal outlet,
   wherein central lumen is configured to receive an epicardial lead translatable therein,
   wherein the hollow tube is an elastically deformable, pre-shaped tube that is relatively more rigid than the sheath of the lead body, and has, in the absence of stress, a first bend in a first curvilinear surface and a second bend in a second curvilinear surface, wherein the span along a length of the hollow tube of the first bend in the first curvilinear surface coincides with the span along the length of the hollow tube of the second bend in the second curvilinear surface, and wherein the first and the second curvilinear surfaces are defined in different planes;

wherein the second bend is a distal orientation bend that orients the central lumen distal outlet so as to direct a retractable anchoring screw at a predetermined acute angle relative to an outer wall of a myocardium, wherein rotation of the lead body in a first direction causes deployment of the screw out of the lead body and additional rotation in the first direction after deployment causes the screw to penetrate a myocardium wall; and wherein the first bend and second bend are within a parallelepiped volume of between $15 \times 10 \times 5$ mm$^3$ and $25 \times 15 \times 5$ mm$^3$, the first bend being proximal of the second bend and having a curvilinear surface with dimensions of 15-25 mm by 10-15 mm, and the second bend having a curvilinear surface in a different plane than the curvilinear surface of the first bend with dimensions of 10-15 mm by no more than 5 mm.

16. The accessory tool of claim 15, wherein the two separate curvilinear surfaces include a first curvilinear surface defined by the first bend in a first plane and a second curvilinear surface defined by the second bend in a second plane, and wherein the first plane is substantially perpendicular to the second plane.

17. The accessory tool of claim 15, wherein the hollow tube is relatively more rigid than a body of the epicardial lead translatable within the central lumen.

18. The accessory tool of claim 15, wherein the different planes of the first and second curvilinear surfaces intersect and form an angle between the planes.

* * * * *